(12) United States Patent
Tanaka et al.

(10) Patent No.: US 8,048,625 B2
(45) Date of Patent: Nov. 1, 2011

(54) METHOD OF EXAMINING INFLAMMATORY DISEASE AND METHOD OF SCREENING REMEDY FOR INFLAMMATORY DISEASE

(75) Inventors: Toshihiro Tanaka, Yokohama (JP); Koichi Ozaki, Yokohama (JP); Aritoshi Iida, Yokohama (JP); Masatsugu Hori, Suita (JP); Yozo Ohnishi, Tokyo (JP); Yusuke Nakamura, Yokohama (JP)

(73) Assignee: Riken, Wako-shi, Saitama (JP)

( * ) Notice: Subject to any disclaimer, the term of this patent is extended or adjusted under 35 U.S.C. 154(b) by 490 days.

(21) Appl. No.: 11/793,716

(22) PCT Filed: Dec. 22, 2005

(86) PCT No.: PCT/JP2005/023634
§ 371 (c)(1),
(2), (4) Date: Apr. 8, 2008

(87) PCT Pub. No.: WO2006/068239
PCT Pub. Date: Jun. 29, 2006

(65) Prior Publication Data
US 2010/0323346 A1 Dec. 23, 2010

(30) Foreign Application Priority Data
Dec. 24, 2004 (JP) .................. 2004-374156

(51) Int. Cl.
*C07H 21/04* (2006.01)
*C12Q 1/68* (2006.01)
(52) U.S. Cl. ....... 435/6.1; 435/6.11; 536/23.1; 536/24.3
(58) Field of Classification Search .................. None
See application file for complete search history.

(56) References Cited

FOREIGN PATENT DOCUMENTS
JP 2002-136291 11/2002

OTHER PUBLICATIONS

Rosmond et al. (J. of Clinical Endocrinology and Metabolism, vol. 85, No. 9, pp. 2000).*
Clement et al. (Nature, vol. 392, pp. 398-401, Mar. 1998).*
Hansel et al. Eur Respir. Journal, vol. 34, pp. 103-110, 2009).*
Liu Y. J- et al., Physiol. Genomics, Apr. 2004, vol. 17, No. 2, pp. 101-106.
Ozaki, K. et al., Nature, May 2004, vol. 429, No. 6987, pp. 72 to 75.
Braunwald, E., "Shattuck Lecture—Cardiovascular medicine at the turn of the millennium: triumphs, concerns, and opportunities," New England Jo Med, 1997, vol. 337, No. 19, pp. 1360-1369.
Breslow, J., "Cardiovascular disease burden increases, NIH funding decreases," Nature Medicine, 1997, vol. 3, No. 6, pp. 600-601.
Gitt, M. et al., "Galectin-2, galectins-5 and-9, and galectins-4 and-6,", Trends in Glycoscience and Glycotechnology, 1997, vol. 9, No. 45, pp. 87-93.
Liu, Y. et al., "Test of linkage and/or association of the LEPR gene polymorphisms with obesity phenotypes in Caucasian nuclear families", Physiol Genomics, 2004, vol. 17, No. 2, pp. 101-106.
Ozaki, K. et al, "Functional SNPs in the lymphotoxin-alpha gene that are associated with susceptibility to myocardial infarction," Nature Genetics, 2002, vol. 32, pp. 650-654.
Ozaki, K. et al., "Functional variation in LGALS2 confers risk of myocardial infarction and regulates lymphotoxin-alpha secretion in vitro," Nature, 2004, vol. 429, No. 6987, pp. 72-75.
Quinton, N. et al, "A single nucleotide polymorphism (SNP) in the leptin receptor is associated with BMA, fat mass, and leptin levels in postmenopausal Caucasian women," Hum Genet, 2001, vol. 108, pp. 233-236.
Tartaglia, L. et al, "Identification and expression cloning of a leptin receptor, OB-R," Cell, 1995, vol. 83, pp. 1263-1271.

* cited by examiner

*Primary Examiner* — Jeanine A Goldberg
(74) *Attorney, Agent, or Firm* — Birch, Stewart, Kolasch & Birch, LLP

(57) ABSTRACT

A single nucleotide polymorphism occurring on a leptin receptor gene is analyzed and an inflammatory disease is examined on the basis of the analytical data. Further, a substance capable of changing the interaction between the leptin receptor and galectin-2 is selected to thereby screen a remedy for an inflammatory disease.

2 Claims, 1 Drawing Sheet

SEQUENCE LISTING

```
<160> NUMBER OF SEQ ID NOS: 22

<210> SEQ ID NO 1
<211> LENGTH: 1265
<212> TYPE: DNA
<213> ORGANISM: Homo sapiens
<220> FEATURE:
<221> NAME/KEY: misc_feature
<222> LOCATION: (164)
<223> OTHER INFORMATION: n = a or g

<400> SEQUENCE: 1
tggccttggt tacctgcaaa ctttgaggcc ccaaggcaca aaaataatag ctttttttt      60 ttattttttt ttttaaggtt catgaaagct tcggacacaa aagcttatat ggtcttcgtc     120
tctataaata aaccagggag taaagaaaaa ccccgctagt ttcngtaaag cgttgctatt     180
aagcaaagca aacctatgca aatatcaagt tcttaatgag gagtgtttcc taaggggcct     240
gtcctctggt accccgcctc tcctctgcca cagtcatgtg aaggcagaca ggcacacact     300
cgcacactag cacgcacttg ggagctcagg aacataaca ctggttagtg agtcggtgtc      360
cctctcccat cgattgcaac ttttcccctc cttccctctc ctgcctctcc ccactttcta     420
catctccgtt ctcaggaagg ctcagggagg atcccccgct gcgtgcactg cgttctgaga     480
ggccggggag agactctggg cccgcggtcg gggcggagcc aaggtcccaa cccacattga     540
acgggcttga ggattacttg gagggctcag gatctaggag gagggcccag ggcactgggt     600
tggggttact ctgggaaagc tctgtgggac caggtgggac cttagggctg gagatggact     660
ctgcgagctg gggcggagt tctagactgg caggagcgga gttctgggtg gcgggggcgg      720
ggtcgggacc agcagggacg gcctctgaga gttgggggcg gaattctggg ccggtgaggg     780
ctgggcgggg accagcaggg gaggcctccg cgagctaggg gaggagctct gcattgtctg     840
gggcggggct tcgagtagcg gtagcgaggt ctggagccgc aggcgctgcc tccgcgaggt     900 agggaggag ctctgtactg tcaggggcgg ggctctgagt agcgaggccg ggtctgaact      960
atcaggcgcg gcctctgcga gctggggggcg gggttctgca ccggcggggg cggggttgtg    1020
agtggtgggg gcggggtctg gagcagcagg cgccgcgttt gcgagctaag gtcggagttc    1080
tgcaccggcg ggggcggggc tctgcgtggc cggggcgggc tcgggatccg cggggcgact    1140
cccggtctgg cttgggcagg ctgcccgggc cgtggcagga agccggaagc agccgcggcc    1200
ccagttcggg agacatggcg ggcgttaaag gtacatcgcg gtccccggct cgctcgtcgt    1260
gtggt                                                              1265

<210> SEQ ID NO 2
<211> LENGTH: 558
<212> TYPE: DNA
```

<213> ORGANISM: Homo sapiens
<220> FEATURE:
<221> NAME/KEY: misc_feature
<222> LOCATION: (377)
<223> OTHER INFORMATION: n = c or t

<400> SEQUENCE: 2

```
cccccccagc tctagggacg accacacccc cacccagttc tgcctgtctc tctctgcgcc      60
tttgactctg ttgggtgggg acaaggctcc cgggcctgca ccctcccgca gctctcagca     120
tccctatttg tccaagtgca ccctgaccc tggacttccg agtgcttctg ccctgcagca      180
gcccccacct ctatccttgg ggtttgagct ttgctgtttc agtcaggcag cccccaggag     240
ctgcaagggg agtgtgggtg cttctcttag tccaggccca gctcccctat cctggcctga     300
ctgttgcagg gctcggggtg tgggcacagg ctgctggcag gaggcaggga gccatctcct     360
gatgcttggt gttagangtg tgtgtgcgca gggcacacgt ctgtgagtgt ctgtgtggcg     420
ggcacacctg tcttctgttt cttgtttgag cccctttttgg actgtcctca ctggataacc    480
tcatctccca gagataatgg tctttgtcag tgagagactg atttttttt ttttttttt      540
tttttttgaga cggagtct                                                  558
```

<210> SEQ ID NO 3
<211> LENGTH: 3498
<212> TYPE: DNA
<213> ORGANISM: Homo sapiens
<220> FEATURE:
<221> NAME/KEY: CDS
<222> LOCATION: (1)..(3498)

<400> SEQUENCE: 3

```
atg att tgt caa aaa ttc tgt gtg gtt ttg tta cat tgg gaa ttt att        48
Met Ile Cys Gln Lys Phe Cys Val Val Leu Leu His Trp Glu Phe Ile
1               5                   10                  15 tat gtg ata act gcg ttt aac ttg tca tat cca att act cct tgg aga       96
Tyr Val Ile Thr Ala Phe Asn Leu Ser Tyr Pro Ile Thr Pro Trp Arg
            20                  25                  30 ttt aag ttg tct tgc atg cca cca aat tca acc tat gac tac ttc ctt      144
Phe Lys Leu Ser Cys Met Pro Pro Asn Ser Thr Tyr Asp Tyr Phe Leu
        35                  40                  45 ttg cct gct gga ctc tca aag aat act tca aat tcg aat gga cat tat      192
Leu Pro Ala Gly Leu Ser Lys Asn Thr Ser Asn Ser Asn Gly His Tyr
    50                  55                  60 gag aca gct gtt gaa cct aag ttt aat tca agt ggt act cac ttt tct      240
Glu Thr Ala Val Glu Pro Lys Phe Asn Ser Ser Gly Thr His Phe Ser
65                  70                  75                  80 aac tta tcc aaa aca act ttc cac tgt tgc ttt cgg agt gag caa gat      288
Asn Leu Ser Lys Thr Thr Phe His Cys Cys Phe Arg Ser Glu Gln Asp
                85                  90                  95 aga aac tgc tcc tta tgt gca gac aac att gaa gga aag aca ttt gtt      336
Arg Asn Cys Ser Leu Cys Ala Asp Asn Ile Glu Gly Lys Thr Phe Val
            100                 105                 110 tca aca gta aat tct tta gtt ttt caa caa ata gat gca aac tgg aac      384
Ser Thr Val Asn Ser Leu Val Phe Gln Gln Ile Asp Ala Asn Trp Asn
        115                 120                 125 ata cag tgc tgg cta aaa gga gac tta aaa tta ttc atc tgt tat gtg      432
Ile Gln Cys Trp Leu Lys Gly Asp Leu Lys Leu Phe Ile Cys Tyr Val
    130                 135                 140 gag tca tta ttt aag aat cta ttc agg aat tat aac tat aag gtc cat      480
Glu Ser Leu Phe Lys Asn Leu Phe Arg Asn Tyr Asn Tyr Lys Val His
145                 150                 155                 160 ctt tta tat gtt ctg cct gaa gtg tta gaa gat tca cct ctg gtt ccc      528
```

-continued

| | | |
|---|---|---|
| Leu Leu Tyr Val Leu Pro Glu Val Leu Glu Asp Ser Pro Leu Val Pro<br>165 170 175 | | |
| caa aaa ggc agt ttt cag atg gtt cac tgc aat tgc agt gtt cat gaa<br>Gln Lys Gly Ser Phe Gln Met Val His Cys Asn Cys Ser Val His Glu<br>180 185 190 | 576 | |
| tgt tgt gaa tgt ctt gtg cct gtg cca aca gcc aaa ctc aac gac act<br>Cys Cys Glu Cys Leu Val Pro Val Pro Thr Ala Lys Leu Asn Asp Thr<br>195 200 205 | 624 | |
| ctc ctt atg tgt ttg aaa atc aca tct ggt gga gta att ttc cag tca<br>Leu Leu Met Cys Leu Lys Ile Thr Ser Gly Gly Val Ile Phe Gln Ser<br>210 215 220 | 672 | |
| cct cta atg tca gtt cag ccc ata aat atg gtg aag cct gat cca cca<br>Pro Leu Met Ser Val Gln Pro Ile Asn Met Val Lys Pro Asp Pro Pro<br>225 230 235 240 | 720 | |
| tta ggt ttg cat atg gaa atc aca gat gat ggt aat tta aag att tct<br>Leu Gly Leu His Met Glu Ile Thr Asp Asp Gly Asn Leu Lys Ile Ser<br>245 250 255 | 768 | |
| tgg tcc agc cca cca ttg gta cca ttt cca ctt caa tat caa gtg aaa<br>Trp Ser Ser Pro Pro Leu Val Pro Phe Pro Leu Gln Tyr Gln Val Lys<br>260 265 270 | 816 | |
| tat tca gag aat tct aca aca gtt atc aga gaa gct gac aag att gtc<br>Tyr Ser Glu Asn Ser Thr Thr Val Ile Arg Glu Ala Asp Lys Ile Val<br>275 280 285 | 864 | |
| tca gct aca tcc ctg cta gta gac agt ata ctt cct ggg tct tcg tat<br>Ser Ala Thr Ser Leu Leu Val Asp Ser Ile Leu Pro Gly Ser Ser Tyr<br>290 295 300 | 912 | |
| gag gtt cag gtg agg ggc aag aga ctg gat ggc cca gga atc tgg agt<br>Glu Val Gln Val Arg Gly Lys Arg Leu Asp Gly Pro Gly Ile Trp Ser<br>305 310 315 320 | 960 | |
| gac tgg agt act cct cgt gtc ttt acc aca caa gat gtc ata tac ttt<br>Asp Trp Ser Thr Pro Arg Val Phe Thr Thr Gln Asp Val Ile Tyr Phe<br>325 330 335 | 1008 | |
| cca cct aaa att ctg aca agt gtt ggg tct aat gtt tct ttt cac tgc<br>Pro Pro Lys Ile Leu Thr Ser Val Gly Ser Asn Val Ser Phe His Cys<br>340 345 350 | 1056 | |
| atc tat aag aag gaa aac aag att gtt ccc tca aaa gag att gtt tgg<br>Ile Tyr Lys Lys Glu Asn Lys Ile Val Pro Ser Lys Glu Ile Val Trp<br>355 360 365 | 1104 | |
| tgg atg aat tta gct gag aaa att cct caa agc cag tat gat gtt gtg<br>Trp Met Asn Leu Ala Glu Lys Ile Pro Gln Ser Gln Tyr Asp Val Val<br>370 375 380 | 1152 | |
| agt gat cat gtt agc aaa gtt act ttt ttc aat ctg aat gaa acc aaa<br>Ser Asp His Val Ser Lys Val Thr Phe Phe Asn Leu Asn Glu Thr Lys<br>385 390 395 400 | 1200 | |
| cct cga gga aag ttt acc tat gat gca gtg tac tgc tgc aat gaa cat<br>Pro Arg Gly Lys Phe Thr Tyr Asp Ala Val Tyr Cys Cys Asn Glu His<br>405 410 415 | 1248 | |
| gaa tgc cat cat cgc tat gct gaa tta tat gtg att gat gtc aat atc<br>Glu Cys His His Arg Tyr Ala Glu Leu Tyr Val Ile Asp Val Asn Ile<br>420 425 430 | 1296 | |
| aat atc tca tgt gaa act gat ggg tac tta act aaa atg act tgc aga<br>Asn Ile Ser Cys Glu Thr Asp Gly Tyr Leu Thr Lys Met Thr Cys Arg<br>435 440 445 | 1344 | |
| tgg tca acc agt aca atc cag tca ctt gcg gaa agc act ttg caa ttg<br>Trp Ser Thr Ser Thr Ile Gln Ser Leu Ala Glu Ser Thr Leu Gln Leu<br>450 455 460 | 1392 | |
| agg tat cat agg agc agc ctt tac tgt tct gat att cca tct att cat<br>Arg Tyr His Arg Ser Ser Leu Tyr Cys Ser Asp Ile Pro Ser Ile His<br>465 470 475 480 | 1440 | |
| ccc ata tct gag ccc aaa gat tgc tat ttg cag agt gat ggt ttt tat<br>Pro Ile Ser Glu Pro Lys Asp Cys Tyr Leu Gln Ser Asp Gly Phe Tyr | 1488 | |

```
                Pro Ile Ser Glu Pro Lys Asp Cys Tyr Leu Gln Ser Asp Gly Phe Tyr
                                485                 490                 495 gaa tgc att ttc cag cca atc ttc cta tta tct ggc tac aca atg tgg         1536
Glu Cys Ile Phe Gln Pro Ile Phe Leu Leu Ser Gly Tyr Thr Met Trp
            500                 505                 510 att agg atc aat cac tct cta ggt tca ctt gac tct cca cca aca tgt         1584
Ile Arg Ile Asn His Ser Leu Gly Ser Leu Asp Ser Pro Pro Thr Cys
            515                 520                 525 gtc ctt cct gat tct gtg gtg aag cca ctg cct cca tcc agt gtg aaa         1632
Val Leu Pro Asp Ser Val Val Lys Pro Leu Pro Pro Ser Ser Val Lys
            530                 535                 540 gca gaa att act ata aac att gga tta ttg aaa ata tct tgg gaa aag         1680
Ala Glu Ile Thr Ile Asn Ile Gly Leu Leu Lys Ile Ser Trp Glu Lys
545                 550                 555                 560 cca gtc ttt cca gag aat aac ctt caa ttc cag att cgc tat ggt tta         1728
Pro Val Phe Pro Glu Asn Asn Leu Gln Phe Gln Ile Arg Tyr Gly Leu
                565                 570                 575 agt gga aaa gaa gta caa tgg aag atg tat gag gtt tat gat gca aaa         1776
Ser Gly Lys Glu Val Gln Trp Lys Met Tyr Glu Val Tyr Asp Ala Lys
            580                 585                 590 tca aaa tct gtc agt ctc cca gtt cca gac ttg tgt gca gtc tat gct         1824
Ser Lys Ser Val Ser Leu Pro Val Pro Asp Leu Cys Ala Val Tyr Ala
            595                 600                 605 gtt cag gtg cgc tgt aag agg cta gat gga ctg gga tat tgg agt aat         1872
Val Gln Val Arg Cys Lys Arg Leu Asp Gly Leu Gly Tyr Trp Ser Asn
            610                 615                 620 tgg agc aat cca gcc tac aca gtt gtc atg gat ata aaa gtt cct atg         1920
Trp Ser Asn Pro Ala Tyr Thr Val Val Met Asp Ile Lys Val Pro Met
625                 630                 635                 640 aga gga cct gaa ttt tgg aga ata att aat gga gat act atg aaa aag         1968
Arg Gly Pro Glu Phe Trp Arg Ile Ile Asn Gly Asp Thr Met Lys Lys
                645                 650                 655 gag aaa aat gtc act tta ctt tgg aag ccc ctg atg aaa aat gac tca         2016
Glu Lys Asn Val Thr Leu Leu Trp Lys Pro Leu Met Lys Asn Asp Ser
            660                 665                 670 ttg tgc agt gtt cag aga tat gtg ata aac cat cat act tcc tgc aat         2064
Leu Cys Ser Val Gln Arg Tyr Val Ile Asn His His Thr Ser Cys Asn
            675                 680                 685 gga aca tgg tca gaa gat gtg gga aat cac acg aaa ttc act ttc ctg         2112
Gly Thr Trp Ser Glu Asp Val Gly Asn His Thr Lys Phe Thr Phe Leu
            690                 695                 700 tgg aca gag caa gca cat act gtt acg gtt ctg gcc atc aat tca att         2160
Trp Thr Glu Gln Ala His Thr Val Thr Val Leu Ala Ile Asn Ser Ile
705                 710                 715                 720 ggt gct tct gtt gca aat ttt aat tta acc ttt tca tgg cct atg agc         2208
Gly Ala Ser Val Ala Asn Phe Asn Leu Thr Phe Ser Trp Pro Met Ser
                725                 730                 735 aaa gta aat atc gtg cag tca ctc agt gct tat cct tta aac agc agt         2256
Lys Val Asn Ile Val Gln Ser Leu Ser Ala Tyr Pro Leu Asn Ser Ser
            740                 745                 750 tgt gtg att gtt tcc tgg ata cta tca ccc agt gat tac aag cta atg         2304
Cys Val Ile Val Ser Trp Ile Leu Ser Pro Ser Asp Tyr Lys Leu Met
            755                 760                 765 tat ttt att att gag tgg aaa aat ctt aat gaa gat ggt gaa ata aaa         2352
Tyr Phe Ile Ile Glu Trp Lys Asn Leu Asn Glu Asp Gly Glu Ile Lys
            770                 775                 780 tgg ctt aga atc tct tca tct gtt aag aag tat tat atc cat gat cat         2400
Trp Leu Arg Ile Ser Ser Ser Val Lys Lys Tyr Tyr Ile His Asp His
785                 790                 795                 800 ttt atc ccc att gag aag tac cag ttc agt ctt tac cca ata ttt atg         2448
```

```
              Phe Ile Pro Ile Glu Lys Tyr Gln Phe Ser Leu Tyr Pro Ile Phe Met
                              805                 810                 815 gaa gga gtg gga aaa cca aag ata att aat agt ttc act caa gat gat          2496
Glu Gly Val Gly Lys Pro Lys Ile Ile Asn Ser Phe Thr Gln Asp Asp
                820                 825                 830 att gaa aaa cac cag agt gat gca ggt tta tat gta att gtg cca gta          2544
Ile Glu Lys His Gln Ser Asp Ala Gly Leu Tyr Val Ile Val Pro Val
            835                 840                 845 att att tcc tct tcc atc tta ttg ctt gga aca tta tta ata tca cac          2592
Ile Ile Ser Ser Ser Ile Leu Leu Leu Gly Thr Leu Leu Ile Ser His
        850                 855                 860 caa aga atg aaa aag cta ttt tgg gaa gat gtt ccg aac ccc aag aat          2640
Gln Arg Met Lys Lys Leu Phe Trp Glu Asp Val Pro Asn Pro Lys Asn
865                 870                 875                 880 tgt tcc tgg gca caa gga ctt aat ttt cag aag cca gaa acg ttt gag          2688
Cys Ser Trp Ala Gln Gly Leu Asn Phe Gln Lys Pro Glu Thr Phe Glu
                885                 890                 895 cat ctt ttt atc aag cat aca gca tca gtg aca tgt ggt cct ctt ctt          2736
His Leu Phe Ile Lys His Thr Ala Ser Val Thr Cys Gly Pro Leu Leu
                900                 905                 910 ttg gag cct gaa aca att tca gaa gat atc agt gtt gat aca tca tgg          2784
Leu Glu Pro Glu Thr Ile Ser Glu Asp Ile Ser Val Asp Thr Ser Trp
            915                 920                 925 aaa aat aaa gat gag atg atg cca aca act gtg gtc tct cta ctt tca          2832
Lys Asn Lys Asp Glu Met Met Pro Thr Thr Val Val Ser Leu Leu Ser
        930                 935                 940 aca aca gat ctt gaa aag ggt tct gtt tgt att agt gac cag ttc aac          2880
Thr Thr Asp Leu Glu Lys Gly Ser Val Cys Ile Ser Asp Gln Phe Asn
945                 950                 955                 960 agt gtt aac ttc tct gag gct gag ggt act gag gta acc tat gag gcc          2928
Ser Val Asn Phe Ser Glu Ala Glu Gly Thr Glu Val Thr Tyr Glu Ala
                965                 970                 975 gaa agc cag aga caa ccc ttt gtt aaa tac gcc acg ctg atc agc aac          2976
Glu Ser Gln Arg Gln Pro Phe Val Lys Tyr Ala Thr Leu Ile Ser Asn
                980                 985                 990 tct aaa cca agt gaa act ggt gaa gaa caa ggg ctt ata aat agt tca          3024
Ser Lys Pro Ser Glu Thr Gly Glu Glu Gln Gly Leu Ile Asn Ser Ser
            995                 1000                1005 gtc acc aag tgc ttc tct agc aaa aat tct ccg ttg aag gat tct              3069
Val Thr Lys Cys Phe Ser Ser Lys Asn Ser Pro Leu Lys Asp Ser
        1010                1015                1020 ttc tct aat agc tca tgg gag ata gag gcc cag gca ttt ttt ata              3114
Phe Ser Asn Ser Ser Trp Glu Ile Glu Ala Gln Ala Phe Phe Ile
        1025                1030                1035 tta tca gat cag cat ccc aac ata att tca cca cac ctc aca ttc              3159
Leu Ser Asp Gln His Pro Asn Ile Ile Ser Pro His Leu Thr Phe
        1040                1045                1050 tca gaa gga ttg gat gaa ctt ttg aaa ttg gag gga aat ttc cct              3204
Ser Glu Gly Leu Asp Glu Leu Leu Lys Leu Glu Gly Asn Phe Pro
        1055                1060                1065 gaa gaa aat aat gat aaa aag tct atc tat tat tta ggg gtc acc              3249
Glu Glu Asn Asn Asp Lys Lys Ser Ile Tyr Tyr Leu Gly Val Thr
        1070                1075                1080 tca atc aaa aag aga gag agt ggt gtg ctt ttg act gac aag tca              3294
Ser Ile Lys Lys Arg Glu Ser Gly Val Leu Leu Thr Asp Lys Ser
        1085                1090                1095 agg gta tcg tgc cca ttc cca gcc ccc tgt tta ttc acg gac atc              3339
Arg Val Ser Cys Pro Phe Pro Ala Pro Cys Leu Phe Thr Asp Ile
        1100                1105                1110 aga gtt ctc cag gac agt tgc tca cac ttt gta gaa aat aat atc              3384
```

```
Arg Val Leu Gln Asp Ser Cys Ser His Phe Val Glu Asn Asn Ile
1115                1120                1125 aac tta gga act tct agt aag aag act ttt gca tct tac atg cct    3429
Asn Leu Gly Thr Ser Ser Lys Lys Thr Phe Ala Ser Tyr Met Pro
1130                1135                1140 caa ttc caa act tgt tct act cag act cat aag atc atg gaa aac    3474
Gln Phe Gln Thr Cys Ser Thr Gln Thr His Lys Ile Met Glu Asn
1145                1150                1155 aag atg tgt gac cta act gtg taa                                3498
Lys Met Cys Asp Leu Thr Val
1160                1165

<210> SEQ ID NO 4
<211> LENGTH: 1165
<212> TYPE: PRT
<213> ORGANISM: Homo sapiens

<400> SEQUENCE: 4

Met Ile Cys Gln Lys Phe Cys Val Val Leu Leu His Trp Glu Phe Ile
1               5                   10                  15

Tyr Val Ile Thr Ala Phe Asn Leu Ser Tyr Pro Ile Thr Pro Trp Arg
            20                  25                  30

Phe Lys Leu Ser Cys Met Pro Pro Asn Ser Thr Tyr Asp Tyr Phe Leu
        35                  40                  45

Leu Pro Ala Gly Leu Ser Lys Asn Thr Ser Asn Ser Asn Gly His Tyr
    50                  55                  60

Glu Thr Ala Val Glu Pro Lys Phe Asn Ser Ser Gly Thr His Phe Ser
65                  70                  75                  80

Asn Leu Ser Lys Thr Thr Phe His Cys Cys Phe Arg Ser Glu Gln Asp
                85                  90                  95

Arg Asn Cys Ser Leu Cys Ala Asp Asn Ile Glu Gly Lys Thr Phe Val
            100                 105                 110

Ser Thr Val Asn Ser Leu Val Phe Gln Gln Ile Asp Ala Asn Trp Asn
        115                 120                 125

Ile Gln Cys Trp Leu Lys Gly Asp Leu Lys Leu Phe Ile Cys Tyr Val
    130                 135                 140

Glu Ser Leu Phe Lys Asn Leu Phe Arg Asn Tyr Asn Tyr Lys Val His
145                 150                 155                 160

Leu Leu Tyr Val Leu Pro Glu Val Leu Glu Asp Ser Pro Leu Val Pro
                165                 170                 175

Gln Lys Gly Ser Phe Gln Met Val His Cys Asn Cys Ser Val His Glu
            180                 185                 190

Cys Cys Glu Cys Leu Val Pro Val Pro Thr Ala Lys Leu Asn Asp Thr
        195                 200                 205

Leu Leu Met Cys Leu Lys Ile Thr Ser Gly Gly Val Ile Phe Gln Ser
    210                 215                 220

Pro Leu Met Ser Val Gln Pro Ile Asn Met Val Lys Pro Asp Pro Pro
225                 230                 235                 240

Leu Gly Leu His Met Glu Ile Thr Asp Asp Gly Asn Leu Lys Ile Ser
                245                 250                 255

Trp Ser Ser Pro Pro Leu Val Pro Phe Pro Leu Gln Tyr Gln Val Lys
            260                 265                 270

Tyr Ser Glu Asn Ser Thr Thr Val Ile Arg Glu Ala Asp Lys Ile Val
        275                 280                 285

Ser Ala Thr Ser Leu Leu Val Asp Ser Ile Leu Pro Gly Ser Ser Tyr
    290                 295                 300
```

```
Glu Val Gln Val Arg Gly Lys Arg Leu Asp Gly Pro Gly Ile Trp Ser
305                 310                 315                 320

Asp Trp Ser Thr Pro Arg Val Phe Thr Thr Gln Asp Val Ile Tyr Phe
            325                 330                 335

Pro Pro Lys Ile Leu Thr Ser Val Gly Ser Asn Val Ser Phe His Cys
                340                 345                 350

Ile Tyr Lys Lys Glu Asn Lys Ile Val Pro Ser Lys Glu Ile Val Trp
        355                 360                 365

Trp Met Asn Leu Ala Glu Lys Ile Pro Gln Ser Gln Tyr Asp Val Val
    370                 375                 380

Ser Asp His Val Ser Lys Val Thr Phe Phe Asn Leu Asn Glu Thr Lys
385                 390                 395                 400

Pro Arg Gly Lys Phe Thr Tyr Asp Ala Val Tyr Cys Cys Asn Glu His
                405                 410                 415

Glu Cys His His Arg Tyr Ala Glu Leu Tyr Val Ile Asp Val Asn Ile
                420                 425                 430

Asn Ile Ser Cys Glu Thr Asp Gly Tyr Leu Thr Lys Met Thr Cys Arg
        435                 440                 445

Trp Ser Thr Ser Thr Ile Gln Ser Leu Ala Glu Ser Thr Leu Gln Leu
450                 455                 460

Arg Tyr His Arg Ser Ser Leu Tyr Cys Ser Asp Ile Pro Ser Ile His
465                 470                 475                 480

Pro Ile Ser Glu Pro Lys Asp Cys Tyr Leu Gln Ser Asp Gly Phe Tyr
                485                 490                 495

Glu Cys Ile Phe Gln Pro Ile Phe Leu Leu Ser Gly Tyr Thr Met Trp
            500                 505                 510

Ile Arg Ile Asn His Ser Leu Gly Ser Leu Asp Ser Pro Pro Thr Cys
        515                 520                 525

Val Leu Pro Asp Ser Val Val Lys Pro Leu Pro Pro Ser Ser Val Lys
    530                 535                 540

Ala Glu Ile Thr Ile Asn Ile Gly Leu Leu Lys Ile Ser Trp Glu Lys
545                 550                 555                 560

Pro Val Phe Pro Glu Asn Asn Leu Gln Phe Gln Ile Arg Tyr Gly Leu
                565                 570                 575

Ser Gly Lys Glu Val Gln Trp Lys Met Tyr Glu Val Tyr Asp Ala Lys
            580                 585                 590

Ser Lys Ser Val Ser Leu Pro Val Pro Asp Leu Cys Ala Val Tyr Ala
        595                 600                 605

Val Gln Val Arg Cys Lys Arg Leu Asp Gly Leu Gly Tyr Trp Ser Asn
    610                 615                 620

Trp Ser Asn Pro Ala Tyr Thr Val Val Met Asp Ile Lys Val Pro Met
625                 630                 635                 640

Arg Gly Pro Glu Phe Trp Arg Ile Ile Asn Gly Asp Thr Met Lys Lys
                645                 650                 655

Glu Lys Asn Val Thr Leu Leu Trp Lys Pro Leu Met Lys Asn Asp Ser
            660                 665                 670

Leu Cys Ser Val Gln Arg Tyr Val Ile Asn His His Thr Ser Cys Asn
        675                 680                 685

Gly Thr Trp Ser Glu Asp Val Gly Asn His Thr Lys Phe Thr Phe Leu
690                 695                 700

Trp Thr Glu Gln Ala His Thr Val Thr Val Leu Ala Ile Asn Ser Ile
705                 710                 715                 720

Gly Ala Ser Val Ala Asn Phe Asn Leu Thr Phe Ser Trp Pro Met Ser
                725                 730                 735
```

-continued

```
Lys Val Asn Ile Val Gln Ser Leu Ser Ala Tyr Pro Leu Asn Ser Ser
            740                 745                 750
Cys Val Ile Val Ser Trp Ile Leu Ser Pro Ser Asp Tyr Lys Leu Met
            755                 760                 765
Tyr Phe Ile Ile Glu Trp Lys Asn Leu Asn Glu Asp Gly Glu Ile Lys
            770                 775                 780
Trp Leu Arg Ile Ser Ser Val Lys Lys Tyr Tyr Ile His Asp His
785                 790                 795                 800
Phe Ile Pro Ile Glu Lys Tyr Gln Ser Leu Tyr Pro Ile Phe Met
                805                 810                 815
Glu Gly Val Gly Lys Pro Lys Ile Ile Asn Ser Phe Thr Gln Asp Asp
            820                 825                 830
Ile Glu Lys His Gln Ser Asp Ala Gly Leu Tyr Val Ile Val Pro Val
            835                 840                 845
Ile Ile Ser Ser Ser Ile Leu Leu Leu Gly Thr Leu Leu Ile Ser His
            850                 855                 860
Gln Arg Met Lys Lys Leu Phe Trp Glu Asp Val Pro Asn Pro Lys Asn
865                 870                 875                 880
Cys Ser Trp Ala Gln Gly Leu Asn Phe Gln Lys Pro Glu Thr Phe Glu
            885                 890                 895
His Leu Phe Ile Lys His Thr Ala Ser Val Thr Cys Gly Pro Leu Leu
            900                 905                 910
Leu Glu Pro Glu Thr Ile Ser Glu Asp Ile Ser Val Asp Thr Ser Trp
            915                 920                 925
Lys Asn Lys Asp Glu Met Met Pro Thr Thr Val Val Ser Leu Leu Ser
            930                 935                 940
Thr Thr Asp Leu Glu Lys Gly Ser Val Cys Ile Ser Asp Gln Phe Asn
945                 950                 955                 960
Ser Val Asn Phe Ser Glu Ala Glu Gly Thr Glu Val Thr Tyr Glu Ala
            965                 970                 975
Glu Ser Gln Arg Gln Pro Phe Val Lys Tyr Ala Thr Leu Ile Ser Asn
            980                 985                 990
Ser Lys Pro Ser Glu Thr Gly Glu Glu Gln Gly Leu Ile Asn Ser Ser
            995                1000                1005
Val Thr Lys Cys Phe Ser Ser Lys Asn Ser Pro Leu Lys Asp Ser
            1010                1015                1020
Phe Ser Asn Ser Ser Trp Glu Ile Glu Ala Gln Ala Phe Phe Ile
            1025                1030                1035
Leu Ser Asp Gln His Pro Asn Ile Ile Ser Pro His Leu Thr Phe
            1040                1045                1050
Ser Glu Gly Leu Asp Glu Leu Leu Lys Leu Glu Gly Asn Phe Pro
            1055                1060                1065
Glu Glu Asn Asn Asp Lys Lys Ser Ile Tyr Tyr Leu Gly Val Thr
            1070                1075                1080
Ser Ile Lys Lys Arg Glu Ser Gly Val Leu Leu Thr Asp Lys Ser
            1085                1090                1095
Arg Val Ser Cys Pro Phe Pro Ala Pro Cys Leu Phe Thr Asp Ile
            1100                1105                1110
Arg Val Leu Gln Asp Ser Cys Ser His Phe Val Glu Asn Asn Ile
            1115                1120                1125
Asn Leu Gly Thr Ser Ser Lys Lys Thr Phe Ala Ser Tyr Met Pro
            1130                1135                1140
Gln Phe Gln Thr Cys Ser Thr Gln Thr His Lys Ile Met Glu Asn
```

```
                    1145                1150               1155
         Lys Met Cys Asp Leu Thr Val
             1160            1165

<210> SEQ ID NO 5
<211> LENGTH: 399
<212> TYPE: DNA
<213> ORGANISM: Homo sapiens
<220> FEATURE:
<221> NAME/KEY: CDS
<222> LOCATION: (1)..(399)

<400> SEQUENCE: 5 atg acg ggg gaa ctt gag gtt aag aac atg gac atg aag ccg ggg tca      48
Met Thr Gly Glu Leu Glu Val Lys Asn Met Asp Met Lys Pro Gly Ser
1               5                   10                  15 acc ctg aag atc aca ggc agc atc gcc gat ggc act gat ggc ttt gta      96
Thr Leu Lys Ile Thr Gly Ser Ile Ala Asp Gly Thr Asp Gly Phe Val
            20                  25                  30 att aat ctg ggc cag ggg aca gac aag ctg aac ctg cat ttc aac cct     144
Ile Asn Leu Gly Gln Gly Thr Asp Lys Leu Asn Leu His Phe Asn Pro
        35                  40                  45 cgc ttc agc gaa tcc acc att gtc tgc aac tca ttg gac ggc agc aac     192
Arg Phe Ser Glu Ser Thr Ile Val Cys Asn Ser Leu Asp Gly Ser Asn
    50                  55                  60 tgg ggg caa gaa caa cgg gaa gat cac ctg tgc ttc agc cca ggg tca     240
Trp Gly Gln Glu Gln Arg Glu Asp His Leu Cys Phe Ser Pro Gly Ser
65                  70                  75                  80 gag gtc aag ttc aca gtg acc ttt gag agt gac aaa ttc aag gtg aag     288
Glu Val Lys Phe Thr Val Thr Phe Glu Ser Asp Lys Phe Lys Val Lys
                85                  90                  95 ctg cca gat ggg cac gag ctg act ttt ccc aac agg ctg ggt cac agc     336
Leu Pro Asp Gly His Glu Leu Thr Phe Pro Asn Arg Leu Gly His Ser
            100                 105                 110 cac ctg agc tac ctg agc gta agg ggc ggg ttc aac atg tcc tct ttc     384
His Leu Ser Tyr Leu Ser Val Arg Gly Gly Phe Asn Met Ser Ser Phe
        115                 120                 125 aag tta aaa gaa taa                                                 399
Lys Leu Lys Glu
    130

<210> SEQ ID NO 6
<211> LENGTH: 132
<212> TYPE: PRT
<213> ORGANISM: Homo sapiens

<400> SEQUENCE: 6

Met Thr Gly Glu Leu Glu Val Lys Asn Met Asp Met Lys Pro Gly Ser
1               5                   10                  15

Thr Leu Lys Ile Thr Gly Ser Ile Ala Asp Gly Thr Asp Gly Phe Val
            20                  25                  30

Ile Asn Leu Gly Gln Gly Thr Asp Lys Leu Asn Leu His Phe Asn Pro
        35                  40                  45

Arg Phe Ser Glu Ser Thr Ile Val Cys Asn Ser Leu Asp Gly Ser Asn
    50                  55                  60

Trp Gly Gln Glu Gln Arg Glu Asp His Leu Cys Phe Ser Pro Gly Ser
65                  70                  75                  80

Glu Val Lys Phe Thr Val Thr Phe Glu Ser Asp Lys Phe Lys Val Lys
                85                  90                  95

Leu Pro Asp Gly His Glu Leu Thr Phe Pro Asn Arg Leu Gly His Ser
            100                 105                 110
```

His Leu Ser Tyr Leu Ser Val Arg Gly Gly Phe Asn Met Ser Ser Phe
            115                 120                 125

Lys Leu Lys Glu
    130

<210> SEQ ID NO 7
<211> LENGTH: 24
<212> TYPE: DNA
<213> ORGANISM: Artificial sequence
<220> FEATURE:
<223> OTHER INFORMATION: primer

<400> SEQUENCE: 7
gccttggtta cctgcaaact ttga                                          24

<210> SEQ ID NO 8
<211> LENGTH: 19
<212> TYPE: DNA
<213> ORGANISM: Artificial sequence
<220> FEATURE:
<223> OTHER INFORMATION: primer

<400> SEQUENCE: 8
cctgagcctt cctgagaac                                                19

<210> SEQ ID NO 9
<211> LENGTH: 21
<212> TYPE: DNA
<213> ORGANISM: Artificial sequence
<220> FEATURE:
<223> OTHER INFORMATION: primer for leptin receptor

<400> SEQUENCE: 9
ttggttacct gcaaactttg a                                             21

<210> SEQ ID NO 10
<211> LENGTH: 19
<212> TYPE: DNA
<213> ORGANISM: Artificial sequence
<220> FEATURE:
<223> OTHER INFORMATION: primer

<400> SEQUENCE: 10
ctgcgccttt gactctgtt                                                19

<210> SEQ ID NO 11
<211> LENGTH: 20
<212> TYPE: DNA
<213> ORGANISM: Artificial sequence
<220> FEATURE:
<223> OTHER INFORMATION: primer

<400> SEQUENCE: 11
cagtctctca ctgacaaaga                                               20

<210> SEQ ID NO 12
<211> LENGTH: 20
<212> TYPE: DNA
<213> ORGANISM: Artificial sequence
<220> FEATURE:
<223> OTHER INFORMATION: primer for galectin-2

<400> SEQUENCE: 12
cctatcctgg cctgactgtt                                               20

```
<210> SEQ ID NO 13
<211> LENGTH: 26
<212> TYPE: DNA
<213> ORGANISM: Artificial sequence
<220> FEATURE:
<223> OTHER INFORMATION: primer

<400> SEQUENCE: 13
actgagaatt tgtattttca gggtgc                                          26

<210> SEQ ID NO 14
<211> LENGTH: 30
<212> TYPE: DNA
<213> ORGANISM: Artificial sequence
<220> FEATURE:
<223> OTHER INFORMATION: primer

<400> SEQUENCE: 14
aattgcaccc tgaaaataca aattctcagt                                      30

<210> SEQ ID NO 15
<211> LENGTH: 30
<212> TYPE: DNA
<213> ORGANISM: Artificial sequence
<220> FEATURE:
<223> OTHER INFORMATION: primer

<400> SEQUENCE: 15
atcgtcgacc catcaccatc accatcactc                                      30

<210> SEQ ID NO 16
<211> LENGTH: 32
<212> TYPE: DNA
<213> ORGANISM: Artificial sequence
<220> FEATURE:
<223> OTHER INFORMATION: primer

<400> SEQUENCE: 16
atcggtacct cagctgtcca tgtgctggcg tt                                   32

<210> SEQ ID NO 17
<211> LENGTH: 36
<212> TYPE: DNA
<213> ORGANISM: Artificial sequence
<220> FEATURE:
<223> OTHER INFORMATION: primer

<400> SEQUENCE: 17
atcggccatg gaggccatga cgggggaact tgaggt                               36

<210> SEQ ID NO 18
<211> LENGTH: 29
<212> TYPE: DNA
<213> ORGANISM: Artificial sequence
<220> FEATURE:
<223> OTHER INFORMATION: primer

<400> SEQUENCE: 18
atcgtcgact cctttaact tgaaagagg                                        29

<210> SEQ ID NO 19
<211> LENGTH: 41
<212> TYPE: DNA
<213> ORGANISM: Artificial sequence
<220> FEATURE:
<223> OTHER INFORMATION: primer

<400> SEQUENCE: 19
```

```
atcgtcgacg ccaccatgac acaccaaaga atgaaaagct a                    41

<210> SEQ ID NO 20
<211> LENGTH: 29
<212> TYPE: DNA
<213> ORGANISM: Artificial sequence
<220> FEATURE:
<223> OTHER INFORMATION: primer

<400> SEQUENCE: 20
atcggtaccc acagttaggt cacacatct                                  29

<210> SEQ ID NO 21
<211> LENGTH: 29
<212> TYPE: DNA
<213> ORGANISM: Artificial sequence
<220> FEATURE:
<223> OTHER INFORMATION: primer

<400> SEQUENCE: 21
atcgaattct gacgggggaa cttgaggtt                                  29

<210> SEQ ID NO 22
<211> LENGTH: 30
<212> TYPE: DNA
<213> ORGANISM: Artificial sequence
<220> FEATURE:
<223> OTHER INFORMATION: primer

<400> SEQUENCE: 22
atcctcgagt tattcttta acttgaaaga                                  30
```

METHOD OF EXAMINING INFLAMMATORY DISEASE AND METHOD OF SCREENING REMEDY FOR INFLAMMATORY DISEASE

TECHNICAL FIELD

The present invention relates to a method of diagnosing an inflammatory disease such as myocardial infarction, and a method of screening a remedy for an inflammatory disease.

BACKGROUND ART

In recent years, risks of death in coronary diseases such as myocardial infarction have increased with changes in life styles (Non-patent Document 1 or 2). Therefore, a method of diagnosing a critical risk for any of those diseases at an early stage has been expected to be developed.

The possibilities of development of coronary diseases such as myocardial infarction due to genetic predispositions have been suggested in the art. Several methods of diagnosing myocardial infarction on the basis of the presence or absence of a gene mutation have been known in the art. For instance, a method of diagnosing a risk of the onset of myocardial infarction by analyzing the polymorphism of a prostacyclin synthase gene has been known (Patent Document 1). However, for diagnosing more precisely, another method for the diagnosis has been expected to be developed.

A leptin receptor is a single-spanning membrane receptor that transmits a signal of leptin that is involved in regulation of food intake and energy expenditure (Non-patent Document 3). It has been known that polymorphisms in some regions of a gene encoding leption receptor are associated with metabolic diseases such as obesity (Non-patent Document 3). Polymorphisms in several portions of a gene that encodes the leptin receptor have been known to relate to asthma (a polymorphism that replaces Q with R: Non-patent Document 4). However, there is no finding with respect to the relationship between the polymorphism of the leptin receptor gene and inflammatory diseases such as myocardial infarction.

Galectins are proteins having affinities for galactose. In mammals, at present, 10 different galectins are known. Among those, galectin-2 is known to form a noncovalent homodimer composed of a 14 KDa subunit and it is self-aggregated to lose its activity in the absence of a reducing agent. In addition, the details of physiological functions of galectin-2 have not been known even though in many cases the expression of galectin-2 is found in epithelial cells in normal adult human tissues, mainly in the lower part of the small intestine (Non-patent Document 5).

Patent Document 1: JP2002-136291
Non-patent Document 1: Nature Medicine, 1997, vol. 3, p 600-601
Non-patent Document 2: New England Journal of Medicine, 1997, vol. 337, p 1360-1369
Non-patent Document 3: Cell, 1995, vol. 83, p 1263-1271
Non-patent Document 4: Hum Genet., 2001, vol. 108(3), p 233-236
Non-patent Document 5: Trends in Glycoscience and Glycotechnology, 1997, vol. 9, No. 45, p 87-93

DISCLOSURE OF THE INVENTION

An object of the present invention is to provide a method of precisely diagnosing a risk of the onset of an inflammatory disease such as myocardial infarction, or the presence or absence of the onset thereof. Another object of the present invention is to provide a method of screening a remedy for an inflammatory disease, such as myocardial infarction.

The inventors of the present invention have intensively studied for solving the above-mentioned objects. As a result, the inventors of the present invention have found that a single nucleotide polymorphism of a leptin receptor gene is associated with myocardial infarction. In addition, the inventors of the present invention have found that the leptin receptor shows a specific interaction with galectin-2 and thus a remedy for an inflammatory disease, such as myocardial infarction, can be obtained by screening a substance capable of altering the interaction, thereby completed the present invention.

That is, the present invention provides the followings.

(1) A method of diagnosing an inflammatory disease, comprising:
analyzing a single nucleotide polymorphism of a leptin receptor gene, and
diagnosing an inflammatory disease based on a result of the analysis.

(2) The method according to (1), wherein the single nucleotide polymorphism present on the leptin receptor gene is a polymorphism of a nucleotide corresponding to the nucleotide at position 164 of SEQ ID NO: 1.

(3) The method according to (1), further analyzing a single nucleotide polymorphism present on a galectin-2 gene and diagnosing the inflammatory disease based on the results of the analysis of leptin receptor gene and galectin-2 gene.

(4) The method according to (3), wherein the polymorphism of the galectin-2 gene is a polymorphism of a nucleotide corresponding to the nucleotide at position 377 of SEQ ID NO: 2.

(5) The method according to any one of (1) to (4), wherein the inflammatory disease is myocardial infarction.

(6) A probe for diagnosing an inflammatory disease, which comprises a sequence of 10 or more nucleotides in SEQ ID NO: 1 including the nucleotide at position 164, or a complementary sequence thereof.

(7) A primer for diagnosing an inflammatory disease, which is capable of amplifying a region comprising the nucleotide at position 164 of SEQ ID NO: 1.

(8) A method of screening a remedy for an inflammatory disease, comprising the steps of:
adding a pharmaceutical candidate substance into a screening system comprising a leptin receptor and a galectin-2;
measuring an interaction between the leptin receptor and the galectin-2; and
selecting a substance that alters the interaction.

DESCRIPTION OF THE PREFERRED EMBODIMENTS

Figure 1:
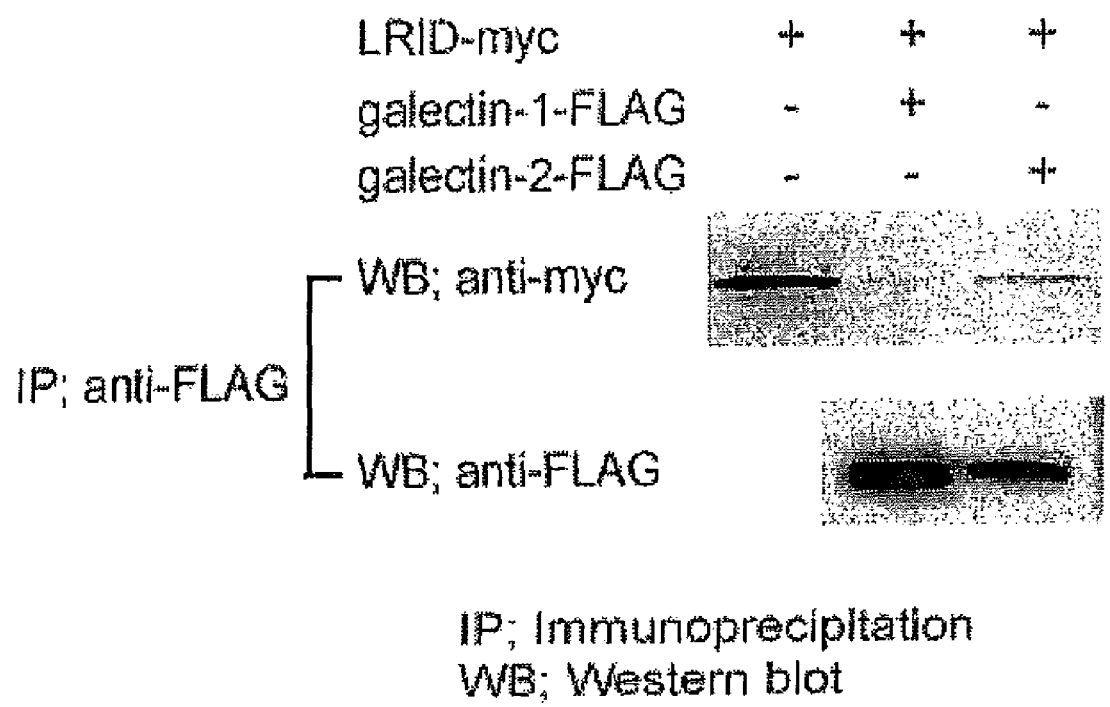
FIG. 1 is a diagram representing the results of immunoprecipitation using an anti-Myc antibody or an anti-FLAG antibody.

<1> Diagnosis Method of the Present Invention

The method of the present invention comprises analyzing a single nucleotide polymorphism associated with an inflammatory disease of a leptin receptor gene, and diagnosing the inflammatory disease based on the analysis. The inflammatory disease is not particularly limited as long as it is one of diseases where the induction of cell adhesion factors and cytokines involved in inflammation is observed, and examples thereof include chronic rheumatism, systemic erythematosus, inflammatory enterocolitis, various kinds of allergosis, bacterial shock, and coronary artery diseases such as myocardial infarction and stroke, and particularly include myocardial infarction. In the present invention, the term "diagnosis" includes diagnosis for a risk of the onset of an inflammatory disease and diagnosis for the presence or absence of the onset.

As a leptin receptor gene, a human leptin receptor gene is preferable. For example, it may be a gene comprising a sequence registered as Accession No. NT_032977 in the database of the National Center for Biotechnology Information (NCBI). In addition, leptin receptor gene is not limited to the gene comprising the above-mentioned sequence because there are racial differences and so on in the gene and substitutions, deletions, or the like may occur in nucleotides other than the nucleotide associated with inflammatory diseases.

Single nucleotide polymorphisms of the leptin receptor gene associated with inflammatory disease are not particularly limited, and an example thereof includes a polymorphism at nucleotide "-978" at the promoter region. The number "-978" is counted from the transcription initiation site. A sequence containing the nucleotide "-978" may be, for example, the sequence of SEQ ID NO: 1. The nucleotide "-978" corresponds to the nucleotide at position 164 of this sequence. In the leptin receptor gene on the human chromosome, there is a polymorphism of adenine (A) and guanine (G) at this nucleotide. By analyzing the polymorphism of this nucleotide, inflammatory diseases can be diagnosed.

The phrase "correspond to" means a corresponding nucleotide in a region containing the above-mentioned sequence on the human leptin receptor gene. Even if the above-mentioned sequence is slightly modified at a position other than the SNP depending on a racial difference or the like, an analysis of the corresponding nucleotide therein may also be included. In addition, the diagnosis may be carried out with respect to a polymorphism adjacent to the leptin receptor gene or in the leptin receptor gene which is in linkage disequilibrium with the above-mentioned single nucleotide polymorphism.

In addition, the sequence of the leptin receptor gene may be analyzed with respect to either of its sense strand or antisense strand.

Samples to be used in analysis of single nucleotide polymorphisms of leptin receptor genes include, but not limited to, body fluid such as urine and blood, cells such as mucous cells, and body hair such as scalp hair. For the analysis of genetic polymorphisms, these samples may be directly used, but preferably chromosomal DNA is isolated from these samples by ordinary methods and then used for the analysis.

The analysis of single nucleotide polymorphisms of leptin receptor gene can be performed by conventional techniques for analyzing the genetic polymorphisms. Examples of the analysis include, but not limited to, sequence analysis, PCR, and hybridization.

The sequencing can be performed by conventional procedures. Specifically, a sequencing reaction is performed using a primer located several tens of nucleotides 5' side from a polymorphic site. From the result of the analysis, the kind of the nucleotide on the corresponding position can be determined. Preferably, when the sequencing is carried out, a fragment containing a polymorphic nucleotide is amplified by PCR or the like.

Further, the analysis can be carried out by detecting the presence of an amplified product in PCR. For instance, primers having a sequence corresponding to a region containing a polymorphic site and corresponding to the respective polymorphic nucleotides are prepared and then used in PCR, followed by detecting the presence of an amplified product to determine the kind of the polymorphic nucleotide.

Further, a DNA fragment containing the polymorphic site may be amplified and the amplified product may be then electrophoresed, followed by determining the kind of the nucleotide based on a difference in mobility. An example of such a method includes single-strand conformation polymorphism (PCR-SSCP) (Genomics. 1992 Jan. 1; 12(1): 139-146). Specifically, at first, a DNA containing a polymorphic site of the leptin receptor gene is amplified and the amplified DNA is then dissociated to single stranded DNAs. Subsequently, the dissociated single stranded DNAs are separated on a non-denaturing gel and the kind of the nucleotide can be then determined based on a difference in mobilities of the dissociated single stranded DNAs on the gel.

Further, when a polymorphic nucleotide is included in a restriction-enzyme recognition sequence, the analysis may depend on the presence or absence of digestion with a restriction enzyme (RFLP method). In this case, at first, a DNA sample is digested with a restriction enzyme. The DNA fragment is then separated, thereby allowing the determination of the kind of the nucleotide based on the size of the detected DNA fragment.

Based on the polymorphism analyzed by the method as described above, a diagnosis of inflammatory disease is carried out.

For instance, in the case of carrying out the diagnosis on the basis of the nucleotide "-978", when the nucleotide is A, it is diagnosed that a risk of the onset of inflammatory disease is high, or a possibility of suffering from inflammatory disease is high. In addition, diagnosis may be performed by considering a polymorphism of an allelic gene. For example, when the genotype is AA allele, it can be diagnosed that a risk of the onset of inflammatory disease is higher, or a possibility of suffering from inflammatory disease is higher, as compared with GG allele.

In the diagnosis method of the present invention, in addition to the polymorphism of the leptin receptor gene, polymorphisms of other genes may be analyzed to determine an inflammatory disease on the basis of a combination of polymorphisms. One of the other genes may be a galectin-2 gene. The sequence of the galectin-2 gene may be one registered as NT_011520 in NCBI. An example of a polymorphism of the galectin-2 gene includes a polymorphism at nucleotide "3279" of intron 1. This nucleotide corresponds to the nucleotide at position 377 of SEQ ID NO: 2. In the human galectin-2 gene, a polymorphism of C and T is present. A risk of inflammatory disease is high in the case of CC as compared with a genotype TT. Therefore, when the polymorphism of the leptin receptor gene is AA and the polymorphism of the galeetin-2 gene is CC, it is diagnosed that a risk of the onset of inflammatory disease is high, or a possibility of suffering from inflammatory disease is high.

Further, in the diagnosis method of the present invention, a diagnosis can also be carried out in combination with polymorphisms of the lymphotoxin a gene which has been known to associate with myocardial infarction ((Nat. Genet. 2002 December; 32(4): 650-4.2002; WO2004/015100).

<2> Diagnosis Agent of the Present Invention

In the present invention, diagnosis agents, such as primers and probes, for diagnosing inflammatory diseases are provided. An example of the probe includes a probe comprising a sequence in SEQ ID NO: 1 including the nucleotide at position 164 or a complementary sequence thereof.

Further, an example of the primer includes: a primer capable of distinguishing a polymorphism of the nucleotide at position 164 of SEQ ID NO: 1, for example, a primer capable of amplifying a region comprising the nucleotide at position 164 of SEQ ID NO: 1. The length of such a primer and a probe is not particularly limited, for instance, an oligonucleotide with a length of 10 to 100 nucleotides is preferable, and an oligonucleotide with a length of 15 to 50 nucleotides is more preferable.

In addition, when used in a sequence analysis, an example of the primer may be one having a 5'-side region from the above-mentioned polymorphic nucleotide, preferably having a sequence of the region 30 to 100 nucleotide upstream from the polymorphic site, or one having a sequence complementary to 3'-side region from the above-mentioned polymorphic nucleotide, preferably having a sequence complementary to the region 30 to 100 nucleotide downstream from the polymorphic site. The primers to be used for determining the polymorphism on the basis of the presence or absence of the amplification in PCR include a primer comprising a sequence including the above-mentioned polymorphic nucleotide on the 3'-side and a primer comprising a sequence complementary to the sequence including the above-mentioned polymorphic nucleotide and containing a nucleotide complementary to the polymorphic nucleotide on the 3'-side.

In addition, the diagnosis agents of the present invention may further comprise PCR polymerase and buffer as well as these primers and probes.

The diagnosis agents of the present invention may further comprise primers and probes for analyzing polymorphisms of the galectin-2 gene. Such a probe includes a probe comprising a sequence of SEQ ID NO: 2 including the nucleotide at position 377 or a complementary sequence thereof, whereas such a primer includes a primer capable of amplifying a DNA comprising a sequence of SEQ ID NO: 2 including the nucleotide at position 377.

<3> Screening Method

The screening method of the present invention is a method for screening a remedy for an inflammatory disease, comprising the steps of: adding a pharmaceutical candidate substance to a screening system comprising a leptin receptor and galectin-2; measuring an interaction between the leptin receptor and the galectin-2; and selecting a substance that alters the interaction.

For leptin receptor and galectin-2, polymorphisms on their respective genes are shown to be associated with inflammatory diseases, such as myocardial infarction, and these proteins specifically interact with each other in vivo. Thus, any substance capable of altering their interaction can be a pharmaceutical candidate substance to inflammatory diseases.

The pharmaceutical candidate substance is not particularly limited, and may be a low-molecular synthetic compound or a compound derived from a natural source. Further, it may be a peptide. Individual test substances or a compound library comprising these substances may be used in screening. Among these candidate substances, a substance that alters the interaction between leptin receptor and galectin-2 is selected as a therapeutic drug for inflammatory disease. Here, the meaning of the term "alter" includes inhibiting the interaction as well as strengthening the interaction.

The screening system comprising leptin receptor and galectin-2 means a screening system comprising both of the proteins and it may be an in vitro system or a cell-based system. The screening system may be a system to which these proteins are directly added or a system where these proteins are to be present by translation of mRNAs transcribed from the corresponding genes.

Specific examples of the in vitro screening system include a pull-down assay using a leptin receptor protein and a galectin-2 protein, and a detection method using surface plasmon resonance as described below.

The leptin receptor protein and galectin-2 protein to be used in in vitro screening system may be recombinant proteins or naturally-occurring proteins. Further, they may be chemically synthesized. Origins of the proteins are not particularly limited, and any protein from eukaryotes including humans and other animals can be used, preferably, a protein of human origin can be used. An example of a leptin receptor protein of human origin includes one comprising the amino acid sequence of SEQ ID NO: 4. Further, as long as it has an affinity with galectin-2, it may have an amino acid sequence of SEQ ID NO: 4 with one- or several-amino acid substitution, deletion, or addition.

On the other hand, an example of a galectin-2 protein of human origin includes one comprising the amino acid sequence of SEQ ID NO: 6. In addition, as long as it has an affinity with leptin receptor, it may have an amino acid sequence of SEQ ID NO: 6 with one- or several-amino acid substitution, deletion, or addition. The term "several" means preferably 2 to 50, more preferably 2 to 20, particularly preferably 2 to 10.

Further, a partial peptide of the protein having a interaction region may be used. The leptin receptor is not always easily expressed because of its large molecular weight, so an intracellular domain (amino acids 864 to 1165 of SEQ ID NO: 4) involved in the interaction with galectin-2 may be used. Alternatively, a protein fused with another peptide may also be used. Peptides to be fused include peptide tags, such as GST, His-tag, and S-tag, which can be used in a pull-down assay and a purification.

For obtaining proteins by gene recombination, for example, DNAs having nucleotide sequences of SEQ ID NO: 3 (leptin receptor) and SEQ ID NO: 5 (galectin-2) are introduced into *E. coli* cells, animal cells, or the like to express the recombinant proteins, followed by purifying the proteins, respectively. Proteins do not always have to be purified, and a partially-purified product or a cell extract may be used in detection of the interaction. Vectors for introducing the above-mentioned DNAs into *E. coli* include pET vector (Novagen) and pGEX vector (Amersham Pharmacia). Vectors for introduction into animal cells include pcDNA vector (Invitrogen).

In the case of carrying out the pull-down assay as an in vitro system, leptin receptor and galectin-2 are incubated in vitro. The interaction between the proteins can be evaluated such that a complex is collected by using an antibody against one of these proteins or an antibody against the peptide tag to be fused or affinity column, followed by detecting the other protein to be bound to that protein. The screening can be carried out such that the test substances are added to the system and any substance that affects the interaction is then selected. In the pull-down assay, one protein may be labeled with a labeling material such as a radioisotope or biotin and then used for the detection.

Further, a system using a biosensor in which a surface plasmon resonance phenomenon is applied can also be exemplified as an in vitro screening system. The biosensor using the surface plasmon resonance phenomenon allows the interaction between the proteins to be observed as a surface plasmon resonance signal in real time with a small amount of protein samples without labeling (e.g., BIAcore, manufactured by Pharmacia). Therefore, the interaction between leptin receptor and galectin-2 may be evaluated using the biosensor, such as BIAcore. Further, the screening of the present invention may be carried out by high through put screening with combinatorial chemistry (Science 1996, 273 p 458-64, Nature 1996, 384 p 11-13).

Further, as another screening system, a system for detection with fluorescence may be used (Fluorescence Resonance Energy Transfer (FRET)).

In addition, the screening can also be carried out in a cell-based system. For example, there may be employed a method using immunoprecipitation. That is, cells expressing leptin receptor and galectin-2 are incubated and then collected, followed by recovering a complex by an antibody directed to one of the proteins. After that, the other one of the proteins is detected by an antibody directed to the protein. Thus, the interaction between the proteins can be detected and the effect of the test sample on the interaction can be evaluated. In this case, both of the proteins may be proteins endogenously expressed in cells, or one or both of them may be proteins exogenously expressed in cells. Examples of the cells to be used include, but not limited to, CHO cells and COS cells.

In the case of exogenously expressing the proteins in animal cells, for example, genes encoding leptin receptor and/or galectin-2 as described above can be expressed by inserting them into vectors for expressing exogenous genes, such as pSV2neo, pcDNA I, and pCD8. In addition, these proteins may be expressed as fusion proteins with peptide tags, such as Myc tag and Flag tag.

The screening system using cells may also employ a two-hybrid method using yeast or animal cells.

In the yeast two-hybrid method, a vector that expresses a fusion protein obtained by fusing one of leptin receptor and galectin-2 or a partial peptide thereof with a GAL4-DNA binding domain is constructed. In addition, a vector that expresses a fusion protein obtained by fusing the other one of the proteins or a partial peptide thereof with a transcription activation domain for VP16, or GAL4 is constructed. Then, these constructed vectors are introduced into yeast cells together with a vector comprising a reporter gene, followed by carrying out an assay of a compound using the reporter activity as an index in the presence of a sample containing a test substance. The interaction between leptin receptor protein and galectin-2 protein induces the expression of a reporter gene. However, the expression of the reporter gene is suppressed when the interaction between the proteins is inhibited by a test compound. Examples of the reporter gene include, but not limited to, an Ade2 gene, a LacZ gene, a CAT gene, a luciferase gene, and a GFP gene, as well as an HIS3 gene. Besides the yeast, the screening by the two-hybrid method can also be carried out using mammalian cells.

The screening by the two-hybrid method can be carried out by using, for example, "MATCHMAKER Two-Hybrid System", "Mammalian MATCHMAKER Two-Hybrid Assay Kit", "MATCHMAKER One-Hybrid System" (each manufactured by TAKARA BIO INC.), or "HybriZAP Two-Hybrid Vector System" (manufactured by Stratagene).

EXAMPLES

Hereinafter, the present invention will be described in more detail. However, the present invention is not limited to these examples.

Example (1) Analysis of Single Nucleotide Polymorphism

Patients suffering from myocardial infarction and those not suffering from myocardial infarction (controls) were respectively subjected to the analysis of the single nucleotide polymorphism in the leptin receptor gene. Specifically, chromosomal DNA isolated from the blood of a test subject was used as a template to carry out PCR with primers of SEQ ID NOs: 7 and 8, thereby amplifying a DNA fragment. A sequence analysis for the polymorphic site was carried out on the resulting amplified product using a primer of SEQ ID NO: 9. For the sequence analysis, the ABI3700 capillary sequencer available from Applied Biosystems was employed. Here, the analyzed patients with myocardial infarction are 2638 individuals (mean age: 63) who have been diagnosed as suffering from myocardial infarction by satisfying at least two of the three conditions (Nat. Genet. 2002 December; 32 (4): 650-4. 2002): (i) having any clinical recording of chest pressure sensation, pain, and oppressive feeling in the chest for 30 minutes or more; (ii) indicating an increase in ST segment larger than 0.1 mV with one standard lead or two precordial leads; and (iii) at least two-fold increase in standard level of serum creatine kinase. The analyzed patients without myocardial infarction are 2,499 individuals (mean age: 51) who have been diagnosed as not suffering from myocardial infarction. The results of the analysis are shown in Table 1.

TABLE 1

| Genotype | | | $\chi^2$ [P value] (Odds ratio) <95% CI> | | | |
|---|---|---|---|---|---|---|
| LEPR promoter −978A > G* | MI | Control | Genotype frequency | Allele frequency | AA vs Others | GG vs Others |
| AA | 1650 (75.6%) | 1732 (70.6%) | 14.7 | 14.1 | 14.7 | 1.35 |
| AG | 488 (22.4%) | 659 (26.9%) | [0.00063] | [0.00018] | [0.00013] | [0.25] |
| GG | 44 (2.0%) | 62 (2.5%) | | (1.25) | (1.29) | (0.79) |
| Total | 2182 (100%) | 2453 (100%) | | <1.11-1.40> | <1.13-1.47> | <0.54-1.17> |

As a result, it was found that a polymorphism of A/G was present at nucleotide "−978" of the promoter region of the leptin receptor gene, and ratio of patients with myocardial infarction were significantly high in major homozygotes (AA alleles) ($\chi^2$=8.4, P=0.0039; odds ratio=1.18) (Table 1). In other words, individuals with AA allele are 1.2 times more likely than others to suffer from myocardial infarction, which statistically corresponds to a significant difference as small as four or less errors per 1,000 tests.

For the patients with myocardial infarction and the individuals without myocardial infarction, the galectin-2 gene was amplified using primers of SEQ ID NOs: 10 and 11 and the resulting amplified product was then analyzed using a primer of SEQ ID NO: 12 with respect to a single nucleotide polymorphism on the galectin-2 gene. As a result, it was found that the polymorphism of C/T was present at nucleotide 3279 of intron 1 and ratio of CC-type was significantly high in the patients of myocardial infarction. In Table 2, the ratio of the polymorphism in the galectin-2 gene and the polymorphism in the leptin receptor gene with respect to patients with myocardial infarction and individuals without myocardial infarction (controls) were shown.

TABLE 2

| Genotype of leptin receptor gene (−978A > G) | | | | | | | |
|---|---|---|---|---|---|---|---|
| | | Genotype of LEPR promoter −978A > G | | | | | |
| | | MI | | | Control | | |
| | | AA | AG | GG | AA | AG | GG |
| Genotype of LGALS2 intron 1 3279C > T | CC | 759 | 233 | 26 | 745 | 270 | 30 |
| | CT | 743 | 213 | 13 | 780 | 290 | 22 |
| | TT | 148 | 42 | 5 | 227 | 99 | 10 |

As a result, ratio of major homozygote (AA allele) of A>G SNP at nucleotide "−978" of the promoter region in the leptin receptor gene is significantly high in patients with myocardial infarction ($\chi^2$=8.4, P=0.0039; odds ratio=1.18) (Table 1).

According to the table, polymorphism of the galectin-2 gene and polymorphism of the leptin receptor gene were combined and the correlations thereof with myocardial infarction were then calculated. As a result, when genotype of the galectin-2 gene is TT and the genotype of the leptin receptor gene is AG or GG, the ratio of myocardial infarction was significantly low as compared to other genotypes (Odds ratio=1.89 (95% c.i.=1.38-2.60), p=0.0000069).

(2) Isolation of Proteins Interacting with Galectin-2 by Using Tandem Affinity Chromatography (Nature Biotechnology, 1999, 17, 1030-1032)

2-1. Construction of Myc-His-TEV-TAP Expression Vector
(i) Insertion of TEV Protease Cleavage Site into pET40b Vector (Manufactured by Novagen)

An oligonucleotide having a nucleotide sequence encoding a TEV protease cleavage site and recognition sequences for restriction enzymes MluI and ScaI (sense strand: SEQ ID NO: 13 and antisense strand: SEQ ID NO: 14) were synthesized and annealed. Then, the pET40b vector was treated with MluI and ScaI restriction enzymes (manufactured by Takara Bio INC.) and purified by using an agarose gel, and then used for insertion of the annealed double-strand DNA. This procedure connected His tag-TEV site-S tag.
(ii) Insertion of the His Tag-TEV Site-S Tag into pCMV-Myc Vector (Manufactured by Clontech)

The His tag-TEV site-S tag sequence in pET40b, which was obtained by the above procedure, was subjected to a PCR amplification with PCR primers (SEQ ID NOs. 15 and 16) added with restriction-enzyme SalI and KpnI sequences. The amplified fragment was treated with SalI and KpnI and then inserted into pCMV-Myc vector similarly treated with SalI and KpnI, to thereby obtain Myc-His-TEV-TAP expression vector.
(iii) Insertion of Galectin-2 into Myc-His-TEV-TAP Expression Vector The galectin-2 was amplified by PCR using galectin-2 amplification primers (SEQ ID: NO: 17 or 18) respectively added with SfiI and SalI sites and using human-lung cDNA (manufactured by Clontech) as a template. The amplified fragment was treated with SfiI and SalI and then inserted into Myc-His-TEV-TAP expression vector, thereby constructing Myc tag-galectin-2-His tag-TEV site-S tag expression vector (hereinafter, also referred to as galectin-TAP vector).

2-2. Introduction of the Galectin-TAP Vector into Cell and Identification of Galectin-2-Binding Protein HeLa cells in a 150-mm dish were transfected with the galectin-TAP vector or only TAP (negative control) using the Fugene agent (manufactured by Roche). Subsequently, the cells were dissolved on ice with a protein extraction reagent (manufactured by Clontech) diluted 10-fold with a S-protein bind/wash buffer (manufactured by Novagen) containing a Complete protease inhibitor tablet (manufactured by Roche) (1 tablet/20 mL) and 5 µg/ml, of MG-132 (manufactured by Calbiochem). An extract was incubated with S-protein agarose (manufactured by Novagen) at 4° C. for 12 to 18 hours to purify a S-tag-binding protein.

Subsequently, the agarose was washed three times with the S-protein bind/wash buffer and then one time with a TEV protease cleavage buffer (10 mM Tris-HCl pH 8.0, 150 mM NaCl, 0.1% Nonidet P-40, 0.5 mM EDTA, and 1 mM DTT). After that, it was incubated with 100 U of TEV protease (manufactured by Invitrogen) at 17° C. for hours, thereby cleaving a TAP-fusion protein (galectin-2). The protein was dialyzed with PBS and then further purified with the TALON affinity purification system (manufactured by Clontech). The resulting protein complex was subjected to SDS-PAGE and then stained with the Simply Blue (Invitrogen). An amino sequence corresponding to the band of the protein was determined using MALDI/TOF mass spectrometry (manufactured by APRO Life Science).

As a result, the sequence was identified as an extracellular domain of the leptin receptor. Consequently, it was found that the leptin receptor binds to galectin-2.

(3) Confirmation of Interaction of Leptin Receptor with Galectin-2

3-1. Construction of Intracellular Domain of Leptin Receptor Fused to FLAG-Tag (LRID-FLAG)

Using primers (SEQ ID NOs: 19 and 20) specific to intracellular domain of the leptin receptor (LRIDs) respectively added with SalI and KpnI sequences were subjected to PCR with human-liver cDNA (manufactured by Clontech) as a template. The amplified fragment was treated with SalI and KpnI and then ligated with a pFLAG-CMV5a vector (manufactured by Sigma) similarly treated with SalI and KpnI, thereby obtaining an expression vector for a FLAG-tag-fused intracellular domain of the leptin receptor.

3-2. Construction of Myc-Tag-Fused Galectin-2 (Galectin-Myc)

Primers (SEQ IDs: 21 and 22) specific to galectin-2 respectively added with Eco RI and XhoI sites were used to carry out PCR with a human-liver cDNA (manufactured by Clontech) as a template. The amplified fragment was treated with EcoRI and XhoI and then ligated with a pCMV-Myc vector (manufactured by Clontech) similarly treated with EcoRI and XhoI, thereby obtaining a Myc-tag-fused galectin-2 expression vector.

COS7 cells (Health Science Research Resources Bank; JCRB9127) were transfected with the galectin-2-FLAG expression vector and the LRID-Myc expression vector using Fugene. After 24 hours, the cells were dissolved for 1 hour or more using a lysis buffer (20 mM Tris-HCl pH 7.5, 150 mM NaCl, and 0.1% Nonidet P-40) to the extent that the precipitation of insoluble debris did not occur. Immunoprecipitation was carried out using an anti-FLAG-tag M2 agarose (manufactured by Sigma) for 12 to 18 hours at 4° C. The precipitate was washed with a lysis buffer and then visualized using an anti-Myc antibody (manufactured by Santa Cruz Biotechnology Inc.) or an anti-Myc antibody peroxidase conjugate (manufactured by Sigma). Further, an experiment using galectin-1 was carried out as a control experiment. The results are shown in FIG. 1. Immunoprecipitation (IP) was carried out using the FLAG antibody and the resulting precipitate was then subjected to Western blot (WB) with the Myc antibody. As a result, galectin-1-FLAG did not coprecipitate with LRID-Myc, while galectin-2-FLAG was co-precipitated with LRID-Myc. Consequently, it was found that the leptin receptor specifically interacted with galectin-2.

INDUSTRIAL APPLICABILITY

According to the diagnosis method of the present invention, inflammatory diseases such as myocardial infarction can be detected at an early stage, which is useful in the fields of diagnosis and the like. Further, according to the screening method of the present invention, novel medicaments for inflammatory diseases such as myocardial infarction can be obtained, which is useful in medical fields and the like.

The invention claimed is:

1. A method for determining an increased risk of onset of myocardial infarction in a human subject comprising:
   a) Obtaining a nucleic acid sample from the human
   b) Analyzing the A/G SNP polymorphism in the leptin receptor gene at position 164 of SEQ ID NO: 1,
   c) Detecting homozygous AA at the single nucleotide polymorphism, and
   d) Identifying the human subject as having an increased risk of onset of myocardial infarction.

2. A method for determining a decreased risk of onset of myocardial infarction in a human subject comprising:
   a) Obtaining a nucleic acid sample from the human
   b) Analyzing the A/G SNP polymorphism in the leptin receptor gene at position 164 of SEQ ID NO: 1,
   c) Analyzing the C/T SNP polymorphism in the galectin-2 gene at position 377 of SEQ ID NO: 2,
   d) Detecting a G at the leptin receptor SNP and detecting homozygous TT at the galectin-2 gene,
   e) Identifying the human subject as having a decreased risk of onset of myocardial infarction.

* * * * *